(12) United States Patent
Hwang et al.

(10) Patent No.: US 7,737,627 B2
(45) Date of Patent: *Jun. 15, 2010

(54) FLUORENE-BASED COMPOUND AND ORGANIC ELECTROLUMINESCENT DISPLAY DEVICE USING THE SAME

(75) Inventors: Seok-Hwan Hwang, Suwon-si (KR); Seok-Jong Lee, Suwon-si (KR); Young-Kook Kim, Suwon-si (KR); Seung-Gak Yang, Suwon-si (KR); Hee-Yeon Kim, Suwon-si (KR)

(73) Assignee: Samsung Mobile Display Co., Ltd., Yongin (KR)

( * ) Notice: Subject to any disclaimer, the term of this patent is extended or adjusted under 35 U.S.C. 154(b) by 1028 days.

This patent is subject to a terminal disclaimer.

(21) Appl. No.: 11/097,182

(22) Filed: Apr. 4, 2005

(65) Prior Publication Data

US 2005/0221124 A1 Oct. 6, 2005

(30) Foreign Application Priority Data

Apr. 2, 2004 (KR) ................. 10-2004-0022877

(51) Int. Cl.
*H01L 51/54* (2006.01)
*H05B 33/14* (2006.01)
*C09K 11/06* (2006.01)
*C07D 209/82* (2006.01)
*C07C 211/00* (2006.01)
*C07C 15/27* (2006.01)

(52) U.S. Cl. ............. 313/504; 428/690; 428/917; 313/506; 257/40; 257/E51.049; 257/E51.05; 257/E51.051; 548/440; 564/427; 585/26

(58) Field of Classification Search .......... 564/427
See application file for complete search history.

(56) References Cited

U.S. PATENT DOCUMENTS 6,517,957 B1 * 2/2003 Senoo et al. ........... 428/690

(Continued)

FOREIGN PATENT DOCUMENTS

DE  10203328  *  8/2003

(Continued)

OTHER PUBLICATIONS

Thomas et al., Journal of the American Chemical Society, (2001), vol. 123, No. 23, pp. 9404-9411.*

(Continued)

*Primary Examiner*—D. Lawrence Tarazano
*Assistant Examiner*—Brett A Crouse
(74) *Attorney, Agent, or Firm*—H.C. Park & Associates, PLC

(57) ABSTRACT

The present invention relates to an organic electroluminescent (OEL) compound that comprises at least one fluorene derivative and at least one carbazole derivative. The compound has good electrical properties, light emitting properties and charge transport ability, and thus is suitable as a host material suitable for fluorescent and phosphorescent dopants of all colors including red, green, blue, white, etc., and as a charge transport material. An OEL display device that uses an organic layer that includes the OEL compound has a high efficiency, a low voltage, a high luminance, and a long lifespan because it has superior current density.

5 Claims, 3 Drawing Sheets

U.S. PATENT DOCUMENTS

2005/0067951 A1* 3/2005 Richter et al. ............... 313/504

FOREIGN PATENT DOCUMENTS

| JP | 11035532 | 2/1999 |
|---|---|---|
| JP | 11144875 | 5/1999 |
| JP | 2005289914 | 10/2005 |

OTHER PUBLICATIONS

Shen et al., Journal of Materials Chemistry, (2005), Issue 15, pp. 2455-2463.*

Chinese Office Action dated Dec. 26, 2008.

K. R. Justin Thomas, et al.; Green and Yellow Electroluminescent Dipolar Carbazole Derivatives: Features and Benefits of Electron-Withdrawing Segments; Chemistry of Materials, 2002; vol. 14, No. 9; pp. 3852-3859.

K. R. Justin Thomas, et al.; Light-Emitting Carbazole Derivatives: Potential Electroluminescent Material; Journal of the American Chemical Socity; 2001; vol. 123, No. 38; pp. 9404-9411.

* cited by examiner

FLUORENE-BASED COMPOUND AND ORGANIC ELECTROLUMINESCENT DISPLAY DEVICE USING THE SAME

CROSS REFERENCE TO RELATED APPLICATION

This application claims the priority to and benefit of Korean Patent Application No. 10-2004-0022877, filed on Apr. 2, 2004 in the Korean Intellectual Property Office, the disclosure of which is incorporated herein in its entirety by reference.

BACKGROUND OF THE INVENTION

1. Field of the Invention

The present invention relates to a fluorene-based compound and an organic electroluminescent (OEL) display device that uses the same. In particular, the present invention relates to an OtL compound that has a structure that comprises at least one fluorene derivative and at least one carbazole derivative. The present invention also relates to an OEL display device with an organic emission layer or a hole transport layer that includes the OEL compound.

2. Description of the Background

In general, an OEL display device (OEL device) has an anode, a hole transport layer (HTL), an emission layer (EML), an electron transport layer (ETL), and a cathode that are sequentially formed on a substrate. The HTL, the EML, and the ETL are organic thin films.

The OEL device with the structure described above operates as follows. When a voltage is applied to the anode and the cathode, holes injected from the anode migrate to the EML via the HTL. Meanwhile, electrons from the cathode are injected in the EML via the ETL. Carriers are recombined in the EML to generate excitons. When these excitons fall from an excited state to a ground state, they emit light in the EML, which forms an image. The light that is emitted when excitons drop to the ground state from a singlet excitation state is referred to as "fluorescence." The light that is emitted when excitons drop to the ground state from a triplet excitation state is referred to as "phosphorescence." Fluorescence with a probability of the singlet excitation state of 25% (triplet excitation state: 75%) has a low luminous efficiency, whereas phosphorescence using a singlet excitation state of 25% and a triplet excitation state of 75% can theoretically have an internal quantum efficiency of about 100%.

A green and red high-efficiency OEL device has been developed that uses $Ir(ppy)_3$ and PtOEP which are phosphorescent pigments that have heavy elements Ir and Pt with a high spin-orbital coupling energy at their central positions as dopants. These pigments effectively emit light even in a triple state (phosphorescent) OEL. In this type of device, 4,4'-N,N'-dicarbazole biphenyl (CBP) is used as a host. CBP has a low glass transition temperature of 110° C. or less and is easily crystallized. Due to CBP's unstable properties, this OEL device has a short life span of only 150 hours or less and is thus unsuitable for commercial use.

SUMMARY OF THE INVENTION

The present invention provides an organic light emitting compound having at least one fluorene derivative and at least one carbazole derivative as side chains. It is used as a host material because it has electrical stability, good charge transport ability, a high glass transition temperature, is capable of preventing crystallization, and is suitable for use with fluorescent dopants and phosphorescent dopants of all colors including red, green, blue and white colors.

The present invention also provides an OEL device that has improved efficiency, low voltage, high luminance, and a long lifespan due to superior current density that uses an organic layer that includes the host material described above.

Additional features of the invention will be set forth in the description which follows, and in part will be apparent from the description, or may be learned by practice of the invention.

The present invention provides a fluorene-based compound represented by Formula (1) below:

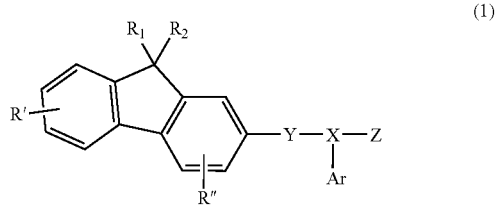

(1)

Z is represented by:

Z =

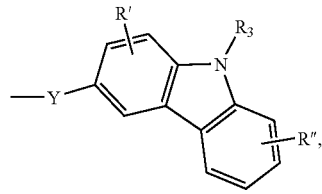

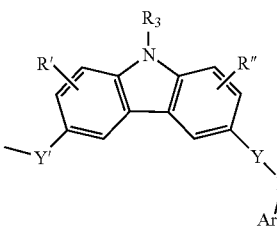

or

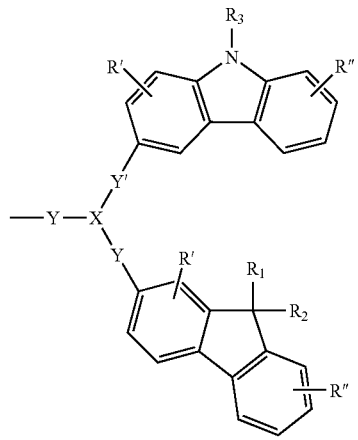

Ar is a substituted or unsubstituted aryl group or a group represented by Formula 2.

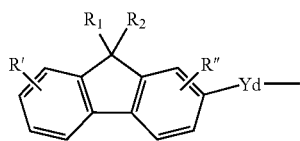

(2)

X is N, B or P. Each of Y and Yd is a single bond, a substituted or unsubstituted C1-C30 alkylene group, a substituted or unsubstituted C6-C30 arylene group, or a substituted or unsubstituted C4-C30 heterocyclic group.

Each of $R_1$, $R_2$ and $R_3$ is a hydrogen atom, a substituted or unsubstituted C1-C30 alkyl group, a substituted or unsubstituted C6-C30 aryl group, a substituted or unsubstituted C4-C30 heterocyclic group, or a substituted or unsubstituted C6-C30 condensed polycyclic group. The neighboring groups among $R_1$, $R_2$ and $R_3$ are connected to each other to form a saturated or unsaturated carbon ring.

Each of R' and R" is a hydrogen, a hydroxy group, a substituted or unsubstituted C1-C30 alkyl group, or a substituted or unsubstituted C6-C30 aryl group.

The present invention also provides an OEL device that includes a pair of electrodes and an organic layer interposed between the electrodes, where the organic layer includes the above-described fluorene-based compound.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE INVENTION

Figure 1:
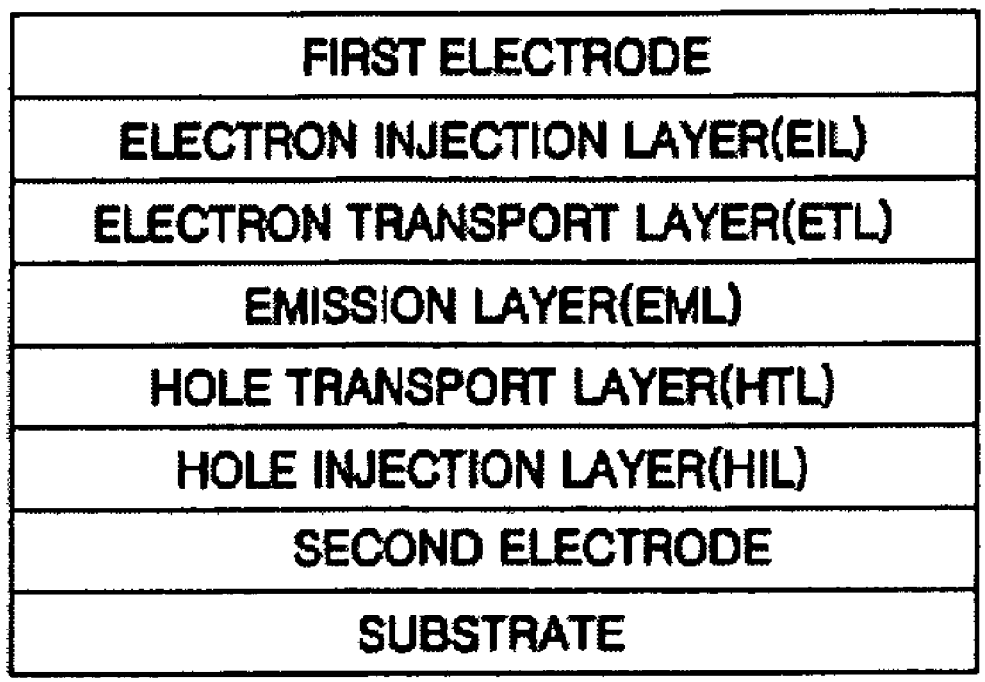
FIG. 1 is a schematic cross-sectional view of an OEL device of the present invention.

A fluorene-based compound represented by Formula (1) of the present invention has a high glass transition temperature (melting point) due to the presence of a rigid carbazole group in its structure. This improves its resistance to heat generated in an organic layer, between the organic layers, and/or between an organic layer and a metal electrode during electroluminescence and the resistance under a high temperature environment. Thus, when this compound is used as a hole transport layer, as an emission material of an OEL device, or as a host material of an emission layer, high luminance and prolonged light emission are also possible.

In particular, a fluorene-based compound with at least two rigid carbazole groups can further improve the above effects. In addition, since the carbazole group improves an energy transition from a singlet excitation state to a triplet excitation state resulting in a smooth energy transfer from the host to the dopant, when the fluorine-based compound is used as a phosphorescent host for green and red phosphorescent dopants, a high efficiency and high luminance OEL device can be obtained.

The fluorene-based compound represented by Formula (1) has a fluorene derivative structure in its molecule which facilitates a singlet transition. Thus, when the fluorene-based compound is used in the emission layer, a high luminance is obtained due to increased fluorescence intensity. When the fluorene-based compound is used as a host for a fluorescent dopant and a phosphorescent dopant, high luminance can also be obtained due to an increased energy transfer to the dopant.

The fluorene-based compound represented by Formula (1) can be used as an emission material, a hole transport material or a hole injection material.

Examples of the fluorene-based compound represented by Formula (1) include the following compounds represented by Formula (3), Formula (4), and Formula (5). These compounds are light emitting materials that have good light-emitting and hole transmission properties and may be used as a blue light emitting material, as green and red phosphorescent and fluorescent host materials, or as a hole transport material.

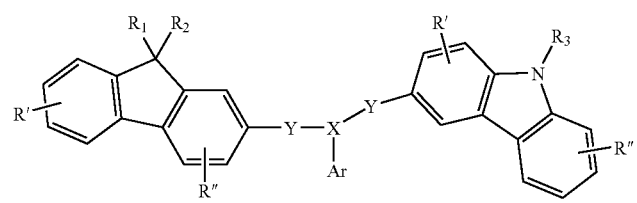

(3)

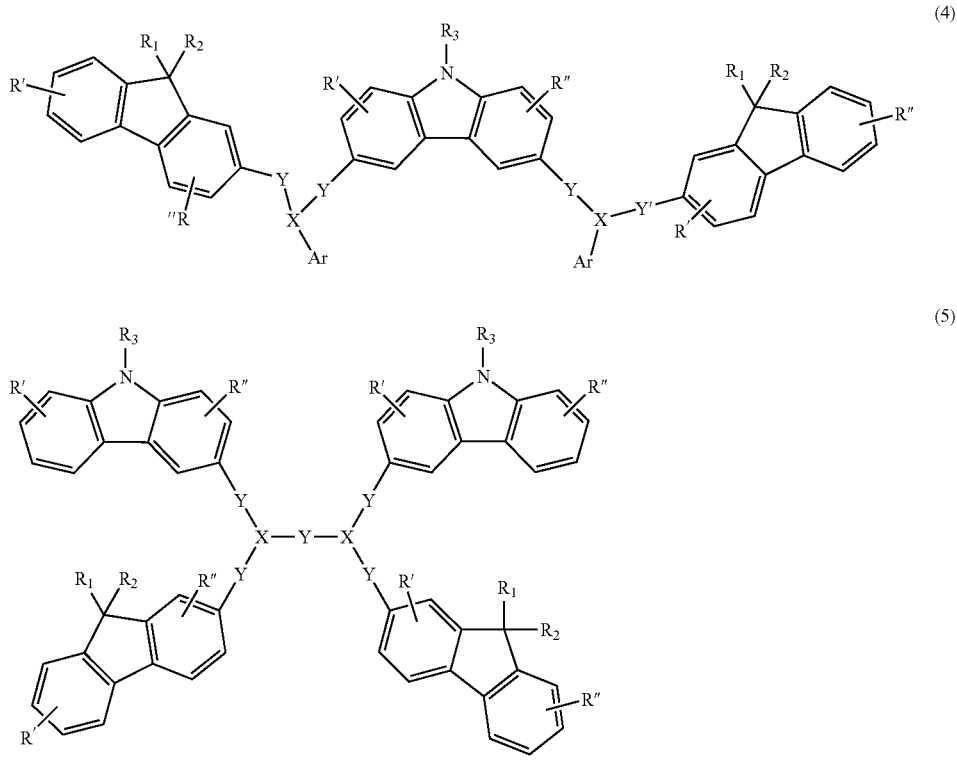

In Formulas (3)-(5), Ar is a substituted or unsubstituted aryl group or a group represented by Formula 2:

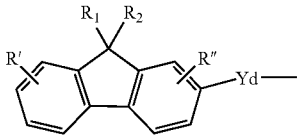

X is N, B or P. Each of Y and Yd is a single bond, or a substituted or unsubstituted C1-C30 alkylene group, a substituted or an unsubstituted C6-C30 arylene group or a substituted or unsubstituted C4-C30 heterocyclic group.

Each of $R_1$, $R_2$ and $R_3$ is a hydrogen, a substituted or an unsubstituted C1-C30 alkyl group, a substituted or unsubstituted C6-C30 aryl group, a substituted or unsubstituted C4-C30 heterocyclic group, or a substituted or unsubstituted C6-C30 condensed polycyclic group, or forms a saturated or unsaturated carbon ring with a neighboring group among the others of $R_1$, $R_2$ and $R_3$.

Each of R' and R" is a hydrogen, a hydroxy group, a substituted or an unsubstituted C1-C30 alkyl group, or a substituted or unsubstituted C6-C30 aryl group.

In the above Formulas (3)-(5), the substituted or unsubstituted aryl group Ar may include, but is not limited to a phenyl group, an ethylphenyl group, an ethylbiphenyl group, o-, m- and p-fluorophenyl groups, a dichlorophenyl group, a dicyanophenyl group, a trifluoromethoxyphenyl group, o-, m- and p-tolyl groups, o-, m- and p-cumenyl groups, a mesityl group, a phenoxyphenyl group, a (α,α-dimethylbenzene) phenyl group, (N,N'-dimethyl)aminophenyl group, a (N,N'-diphenyl) aminophenyl group, a pentalenyl group, an indenyl group, a naphthyl group, a methylnaphthyl group, an anthracenyl group, an azrenyl group, a heptarenyl group, an acenaphthylenyl group, a phenarenyl group, a fluorenyl group, an anthraquinolyl group, a methylanthryl group, a phenanthryl group, a triphenylene group, a pyrenyl group, a crycenyl group, an ethyl-crycenyl group, a picenyl group, a perylenyl group, a chloroperylenyl group, a pentaphenyl group, a pentacenyl group, a tetraphenylene group, a hexaphenyl group, a hexacenyl group, a rubicenyl group, a coroneryl group, a trinaphthylenyl group, a heptaphenyl group, a heptacenyl group, a pyranthrenyl group, an ovarenyl group, a carbazolyl group, etc. Preferably, Ar is a phenyl group, a lower alkylphenyl group, a lower alkoxyphenyl group, a cyanophenyl group, a phenoxyphenyl group, a halophenyl group, a naphthyl group, a lower alkylnaphthyl group, a lower alkoxynaphthyl group, a cyanonaphthyl group, a halonaphthyl group, a fluorenyl group, a carbazolyl group, a lower alkylcarbazolyl group, a biphenyl group, a lower alkylbiphenyl group, a lower alkoxybiphenyl group, a thiophenyl group, an indolyl group or a pyridyl group. The lower alkyl and lower alkoxy groups preferably have 1 to 5 carbon atoms. More preferably, Ar may be a aryl group selected from a fluorenyl group, a carbazolyl group, a phenyl group, a naphthyl group and a phenanthrenyl group, an aromatic ring of which may be substituted by one to three, preferably one C1-C3 lower alkyl, C1-C3 lower alkoxy, cyano, phenoxy, phenyl or halogen atom.

Examples of compounds represented by Formulas (3) to (5) include the following compounds:

7 8
1
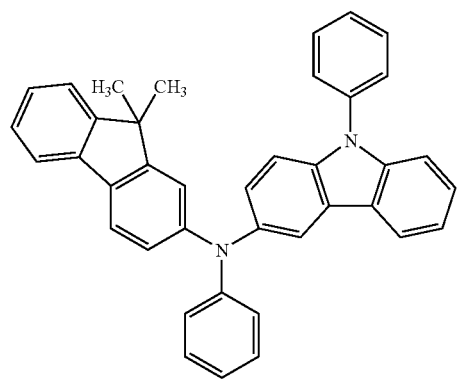
2
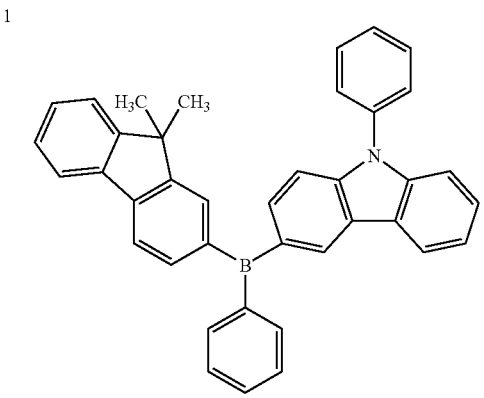
3
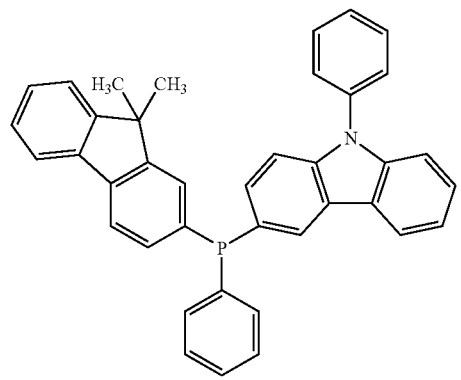
4
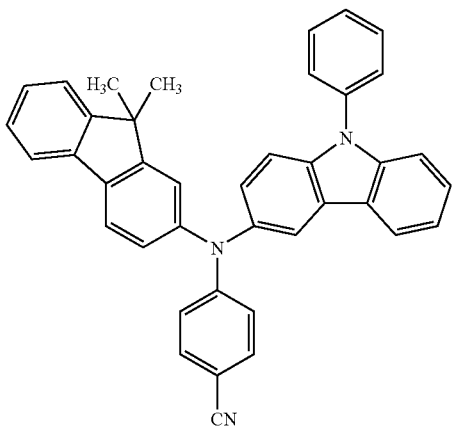
5
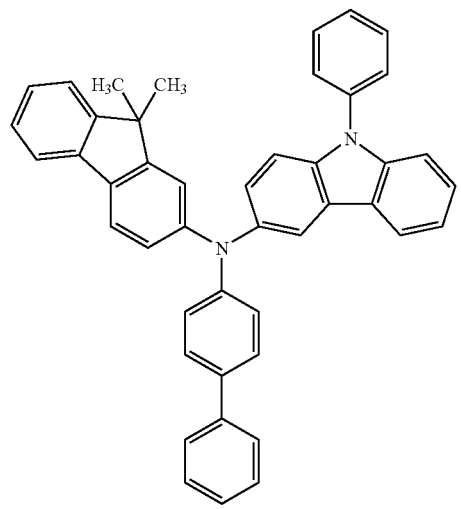
6
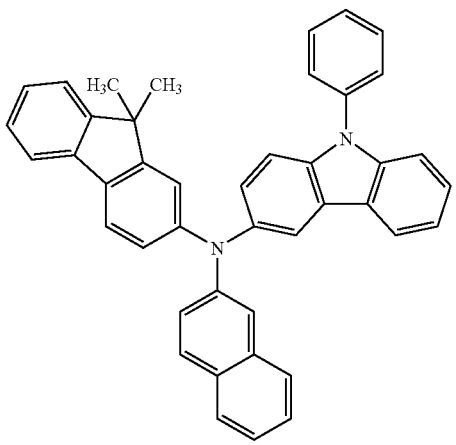

-continued
7
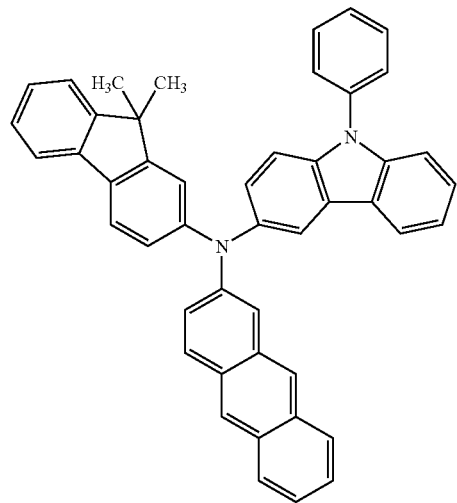
8
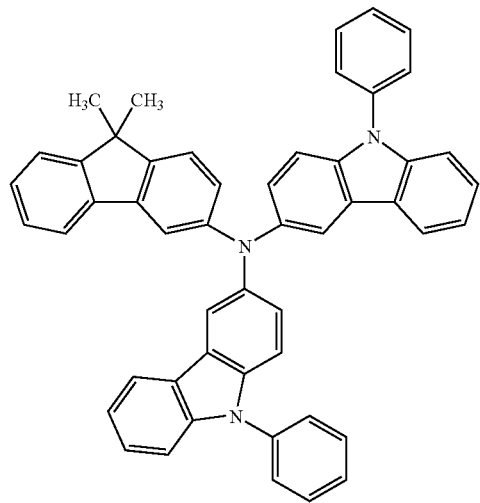
9
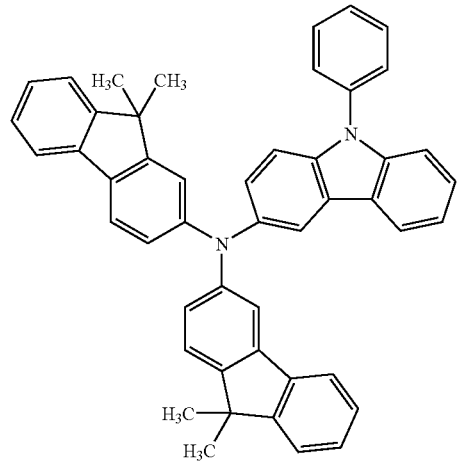
10
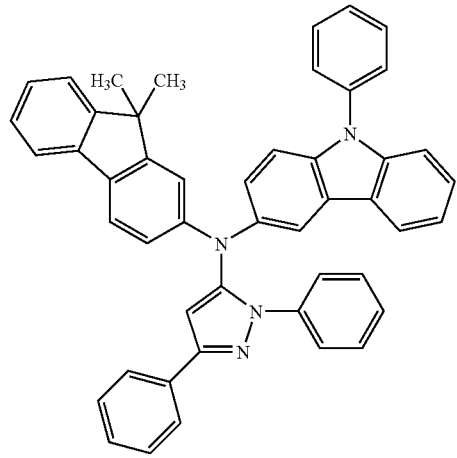
11
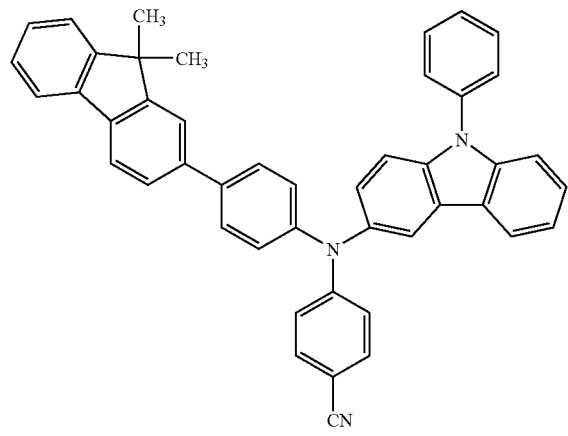
12
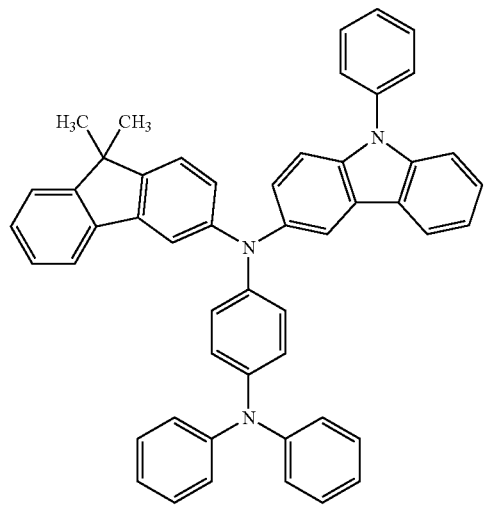

11
13
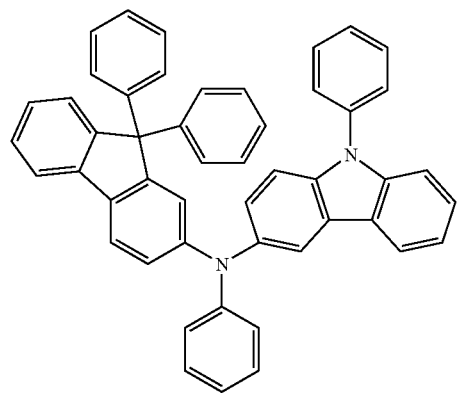
12
14
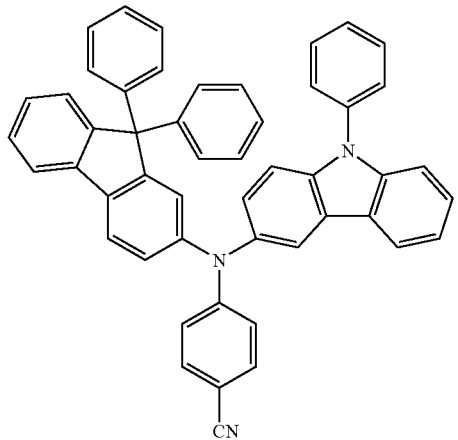
15
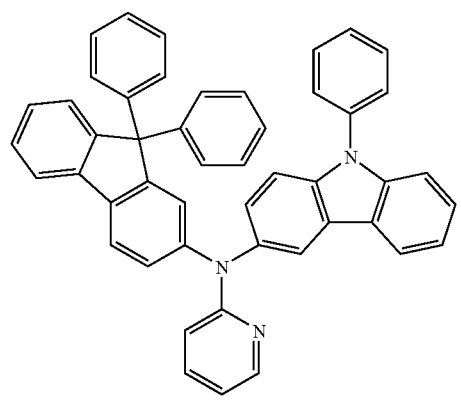
16
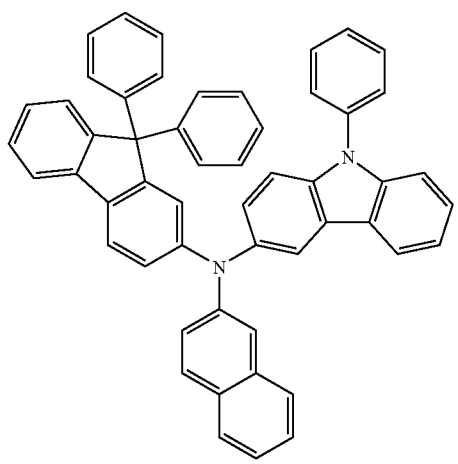
17
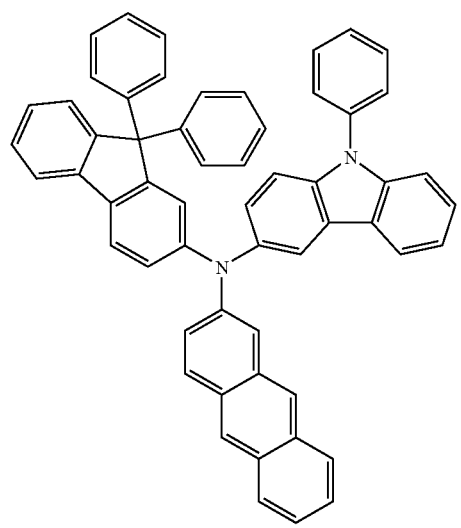
18
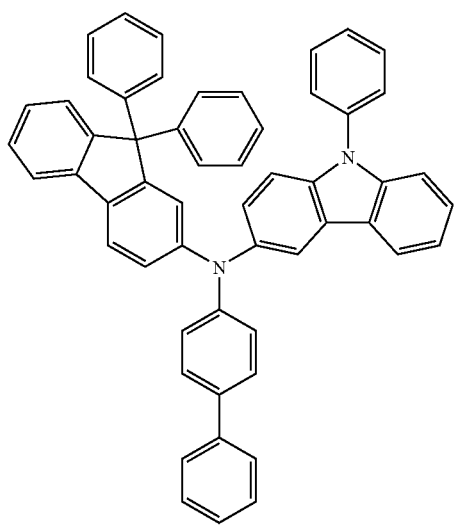

-continued
19
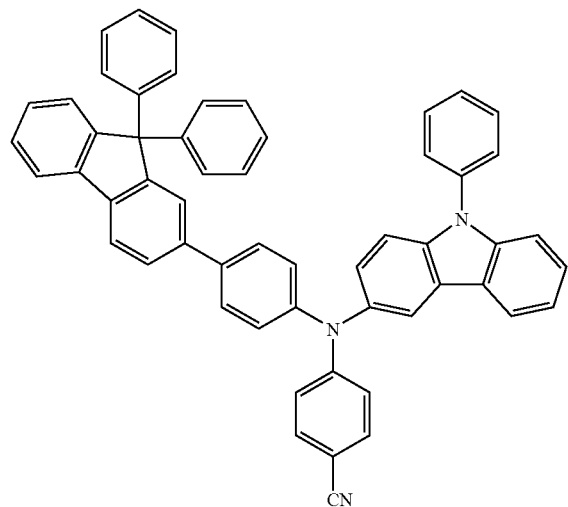
20
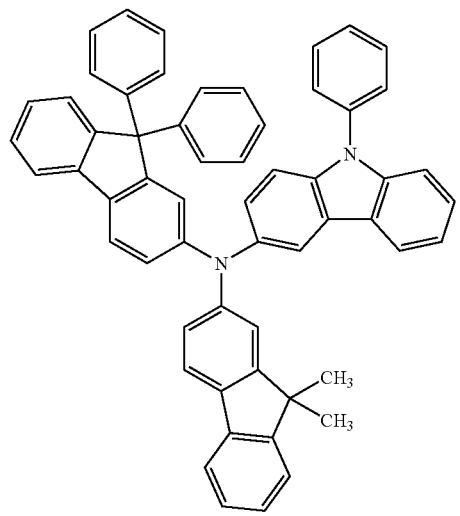
21
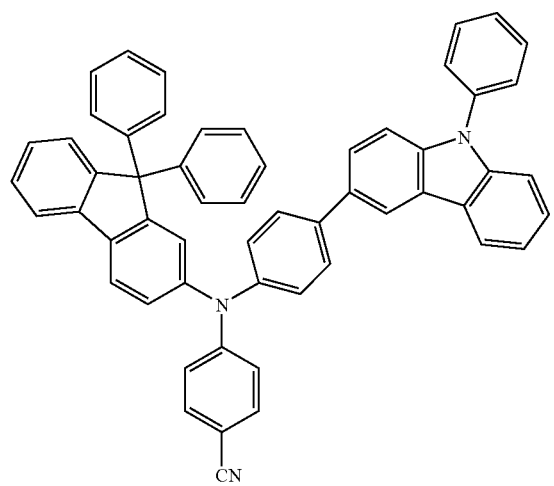
22
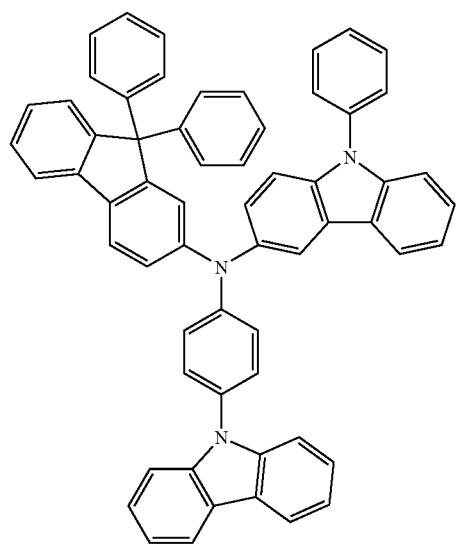

23
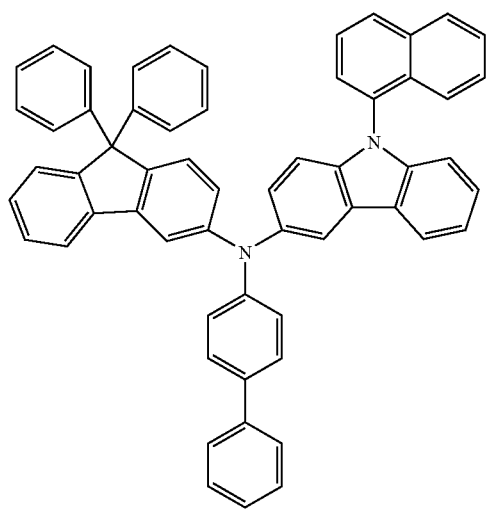
24
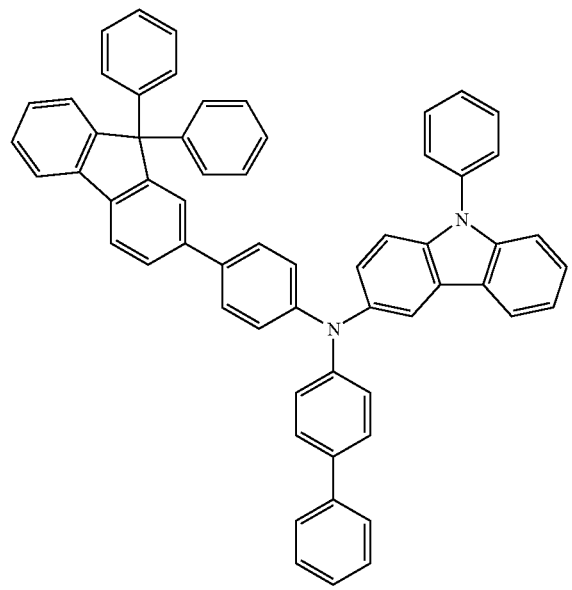
25
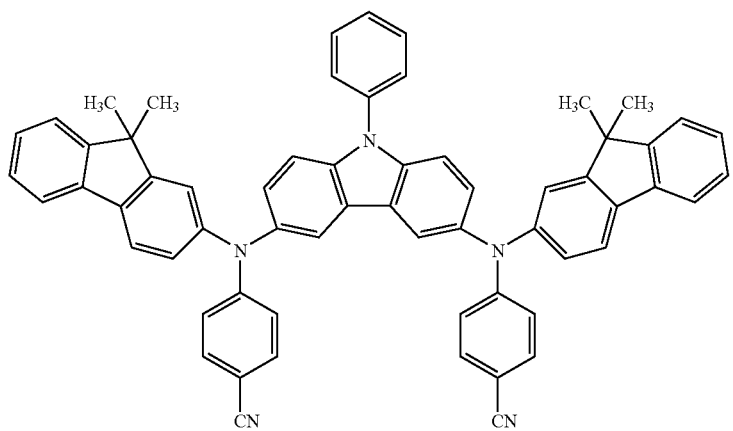
26
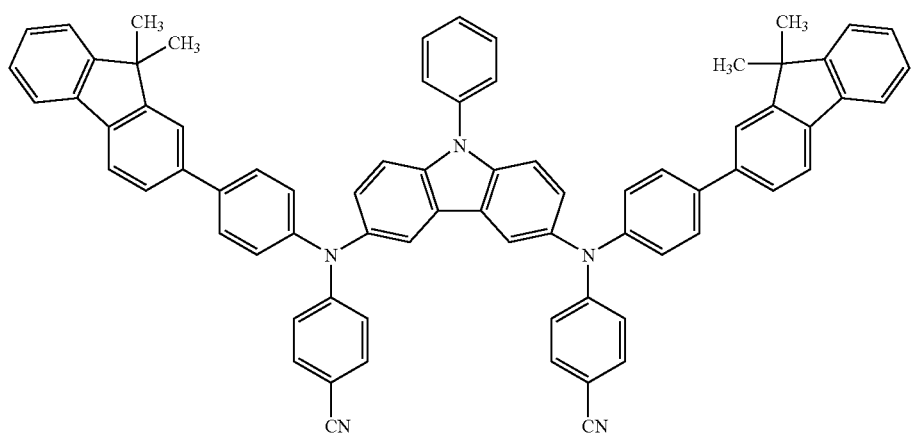

-continued
27
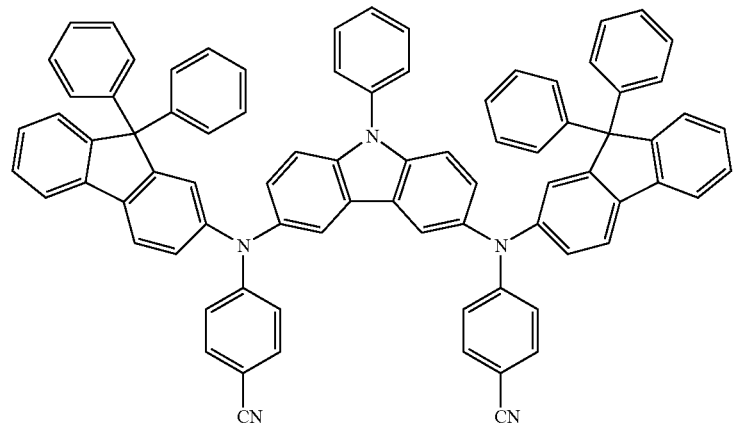
28
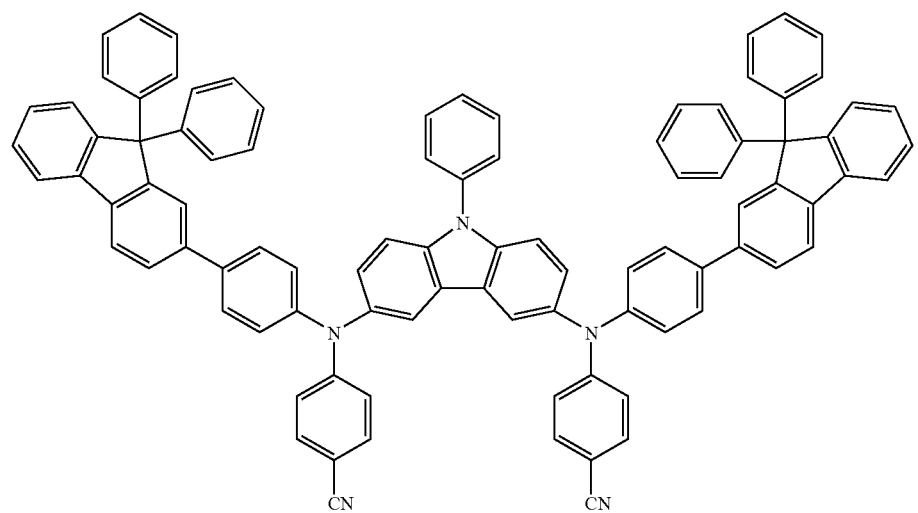
29
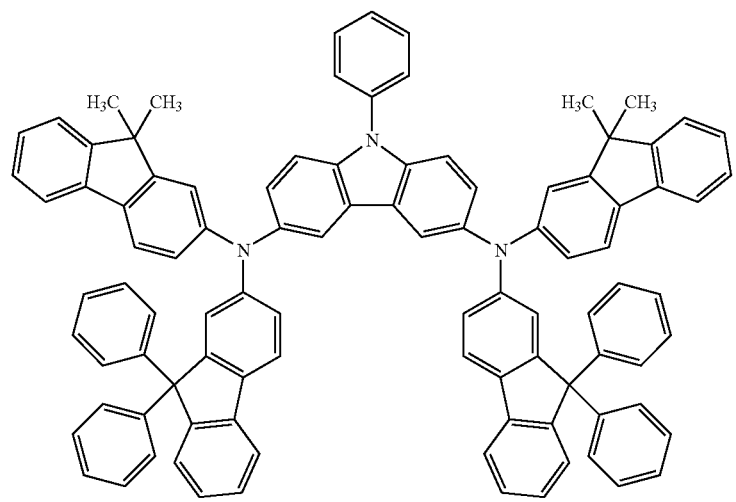

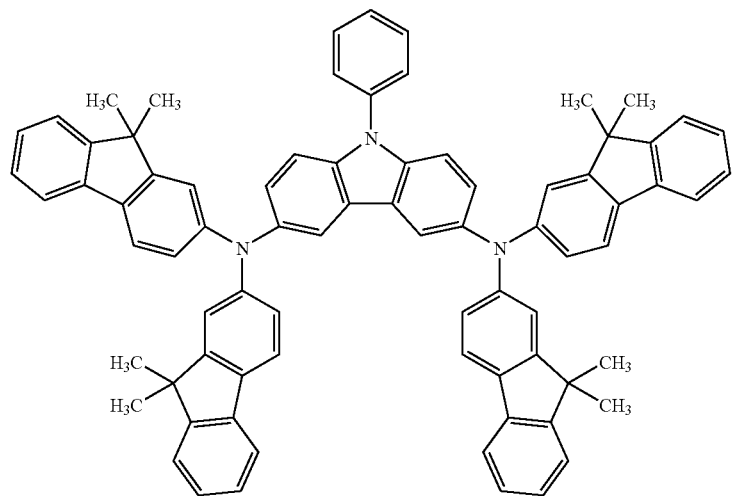
30
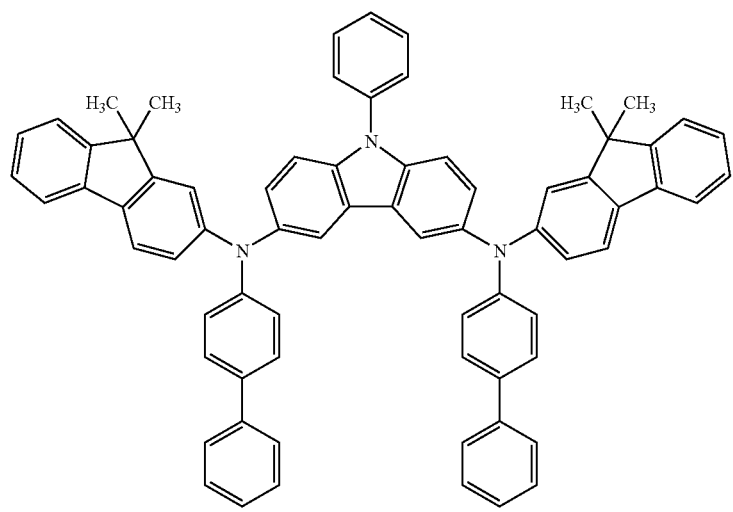
31
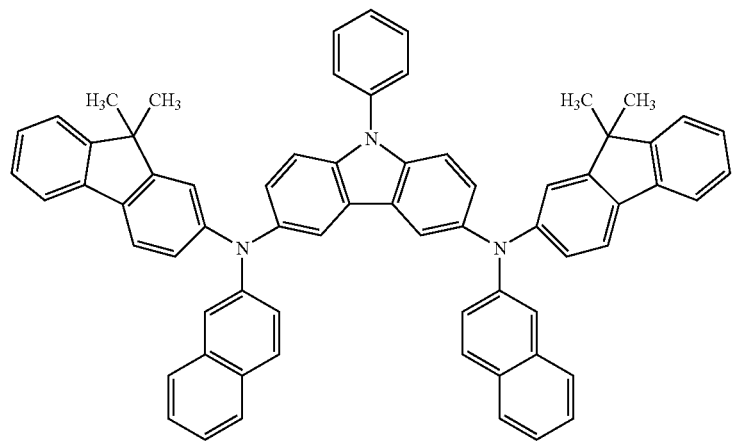
32

33
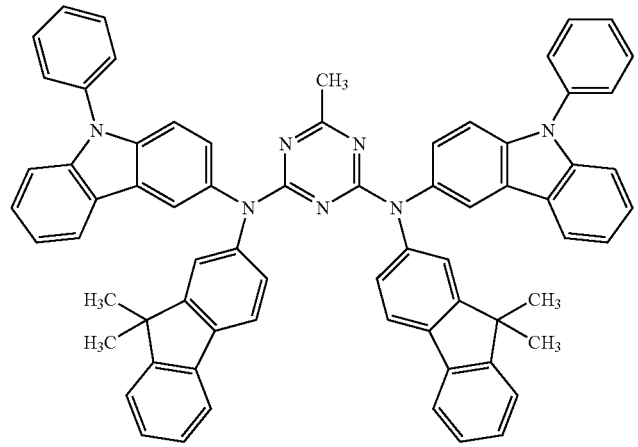
34
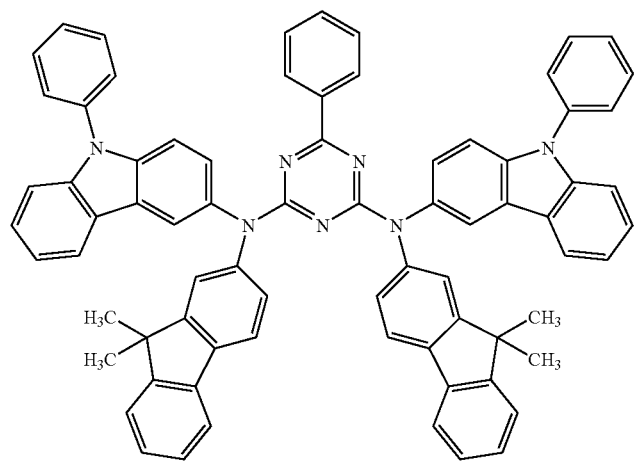
35
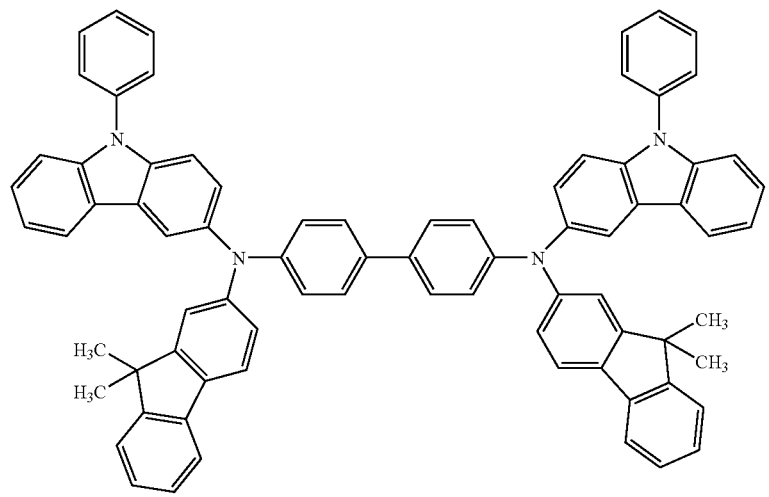

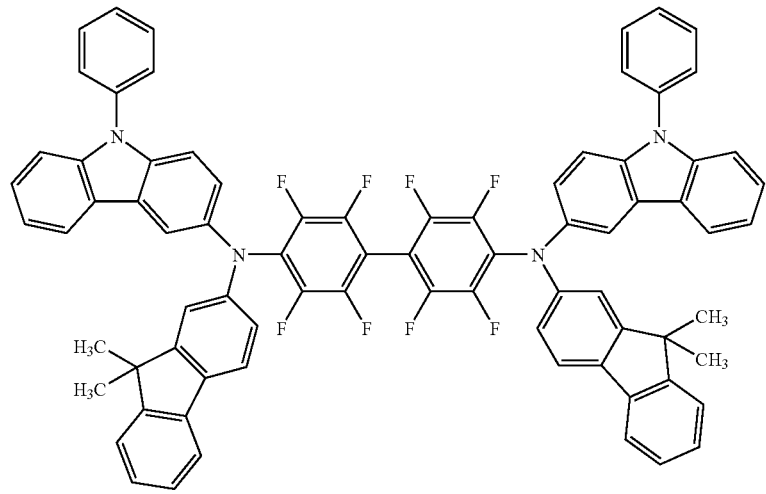

36

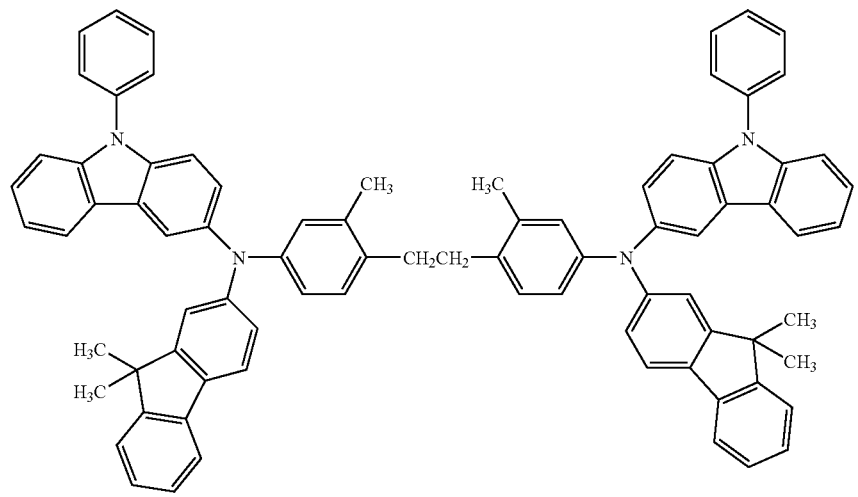

37

The fluorene-based compound represented by Formula (1) is prepared according to the following method where X is N.

Reaction scheme 1

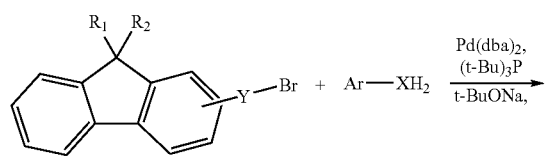

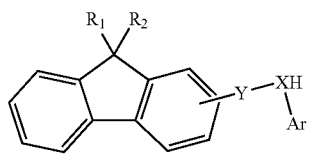

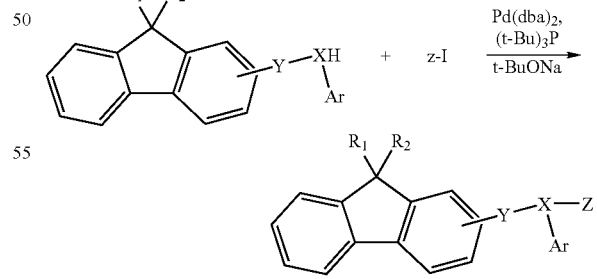

Referring to the reaction scheme 1, brominated fluorene is reacted with Ar—XH2, and then reacted with Z containing iodide, such as Z—I, to obtain the compound represented by Formula (1). In the reaction, Z—I may be replaced with Z—Br, Z—Cl, etc., and brominated fluorene may be replaced with other halogenated fluorene, such as chlorinated fluorene.

A method of preparing an OEL device according to the present invention will now be described.

FIG. 1 is a cross-sectional view of a general OEL device.

First, a first electrode material with a high work function is coated on a substrate by a deposition method or a sputtering method to form a first electrode. Any substrate that is used in a conventional OEL device may be used, and a glass substrate or a transparent plastic substrate that is waterproof, has good mechanical strength, thermal stability, transparency, and surface softness, and can be easily handled is preferable. The first electrode material may be, for example, indium tin oxide (ITO), indium zinc oxide (IZO), tin oxide ($SnO_2$), or zinc oxide (ZnO), which is transparent and has good conductivity.

A hole injection layer (HIL) may be formed on the first electrode by vacuum evaporation, spin-coating, cast, Langmuir-Blodgett (LB), etc. Vacuum evaporation is preferable because it provides a uniform layer and hardly produces a pin hole. When the HIL is formed by vacuum evaporation, the evaporation conditions vary according to a compound used as the HIL material, the desired structure and thermal property of the HIL, but generally have an evaporation temperature of 50 to 500° C., a vacuum pressure of $10^{-8}$ to $10^{-3}$ torr, an evaporation rate of 0.01 to 100 Å/sec, and a layer thickness is selected to be in the range of 10 Å to 5 μm.

The HIL material is not particularly restricted and may include phthalocyanine compounds, such as copper phthalocyanine disclosed in U.S. Pat. No. 4,356,429, the disclosure of which is incorporated herein in its entirety by reference, or a starburst type amine derivative, such as TCTA, m-MTDATA, or m-MTDAPB [Advanced Material, 6, p. 677 (1994)].

A hole transport layer (HTL) is formed on the HIL by vacuum evaporation, spin coating, cast, LB, etc. Again, vacuum evaporation is preferable because it provides a uniform layer and hardly produces a pin hole. When the HTL is formed by the vacuum evaporation, the evaporation conditions vary according to a compound used, but are similar to the evaporation conditions of the HIL. A HTL material is not particularly restricted and may be the fluorene-based compound by the represented by Formula (1) according to the present invention or any known material that is used in the HTL. For example, carbazole derivatives, such as N-phenylcarbazole and polyvinylcarbazole, or conventional amine derivatives having an aromatic condensed ring, such as N,N'-bis(3-methylphenyl)-N,N'-diphenyl-[1,1-biphenyl]-4,4'-diamine (TPD) and N,N'-di(naphthalen-1-yl)-N,N'-diphenyl benzidine (α-NPD) may be used as the HTL material.

An emission layer (EML) is formed on the HTL by vacuum evaporation, spin coating, cast, LB, etc. Again, vacuum evaporation is the preferred method because it provides a uniform layer and hardly produces a pin hole. When the EML is formed by the vacuum evaporation, the evaporation conditions vary according to the compound used, but are similar to the evaporation conditions of the HIL. An EML material is not particularly restricted and the compound represented by Formula (1) of the present invention is used alone or as a host.

When the compound represented by Formula (1) is used as the light-emitting host, the EML may be formed using a phosphorescent or fluorescent dopant together. IDE102 or IDE105 available from Idemitsu may be used as the fluorescent dopant and Ir(ppy)$_3$ (fac tris(2-phenylpyridine) iridium) (green) or FIrpic (iridium(III)bis[4,6-di-(fluorophenyl)-pyridinato-N,C2'] picolinate) (blue) is used as the phosphorescent dopant.

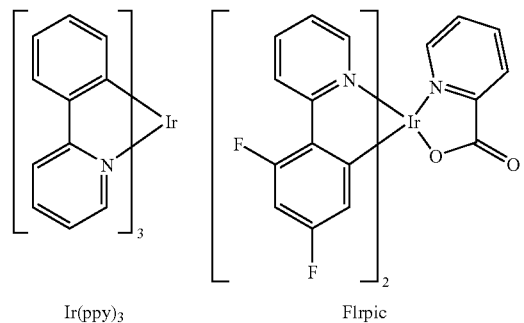

Ir(ppy)$_3$          FIrpic

A red phosphorescent dopant RD61 etc. available from UDC may also be vacuum co-deposited (doped). The concentration of the dopant is not particularly restricted, but may be 0.01 to 15 parts by weight based on 100 parts by weight of a host. When the concentration of the dopant is less than 0.01 parts by weight, it does not sufficiently impart color to the EML. When the concentration of the dopant is greater than 15 parts by weight, an undesirable concentration quenching occurs, which sharply reduces the efficiency.

Further, when the phosphorescent dopant is used in the EML, a hole-blocking material is deposited on the EML by vacuum evaporation or spin-coating to form a hole-blocking layer (HBL), in order to prevent a triplet exciton or a hole from diffusing into an electron transport layer. The hole-blocking material is not particularly restricted and may be any known material that is used as the hole blocking material. For example, an oxadiazole derivative, a triazole derivative, a phenanthroline derivative, or a hole-blocking material described in Japanese Patent Laid-Open Publication No. Hei 11-329734 A1, the disclosure of which is incorporated herein in its entirety by reference, may be used. Typically, Balq represented by the following formula, phenanthrolines (e.g. BCP available from UDC), etc. is used:

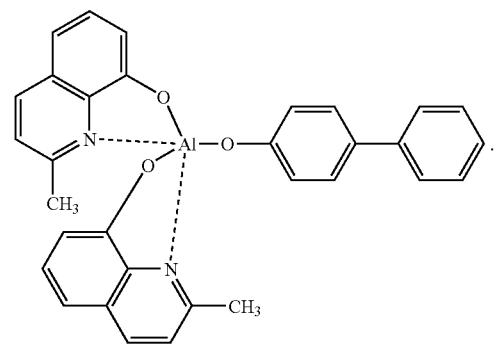

An electron transport layer (ETL) is formed on the EML by vacuum evaporation, spin-coating or cast, preferably vacuum evaporation. An ETL material is not particularly restricted as long as it stably transports electrons injected from a cathode. A quinoline derivative, in particular, aluminum tris(8-quinolinorate) (Alq3) may be used as the ETL material. An electron injection layer (EIL) which facilitates injection of electrons from the cathode may be deposited on the ETL. An EIL material is not particularly restricted, but may be LiF, NaCl, CsF, $Li_2O$, BaO, etc. The deposition conditions of the HBL, ETL, EIL vary according to compounds used, but are similar to the conditions for the HIL.

Finally, a metal is deposited on the EIL using vacuum evaporation or sputtering to form a second electrode. The metal that forms the second electrode may be a metal, an alloy, an electroconductive compound or a mixture thereof that has a low work function, for example, Li, Mg, Al, Al—Li, Ca, Mg—In, Mg—Ag, etc. Furthermore, to obtain a top-emission device, a transmittance type cathode composed of ITO or IZO may be used.

The OEL device according to the present invention may include one or two intermediate layers in addition to the anode (first electrode), the HIL, the HTL, the EML, the ETL, the EIL, and the cathode illustrated in FIG. 1. Even though the HIL, the EIL and the HBL are not required, they can improve the luminous efficiency.

The present invention will be described in greater detail with reference to the preferable Synthesis Examples of the compound represented by Formula 1 that has at least one fluorene derivative and at least one carbazole derivative as side chains. The following examples are for illustrative purposes and are not intended to limit the scope of the invention.

EXAMPLE 1

Reaction Scheme 2

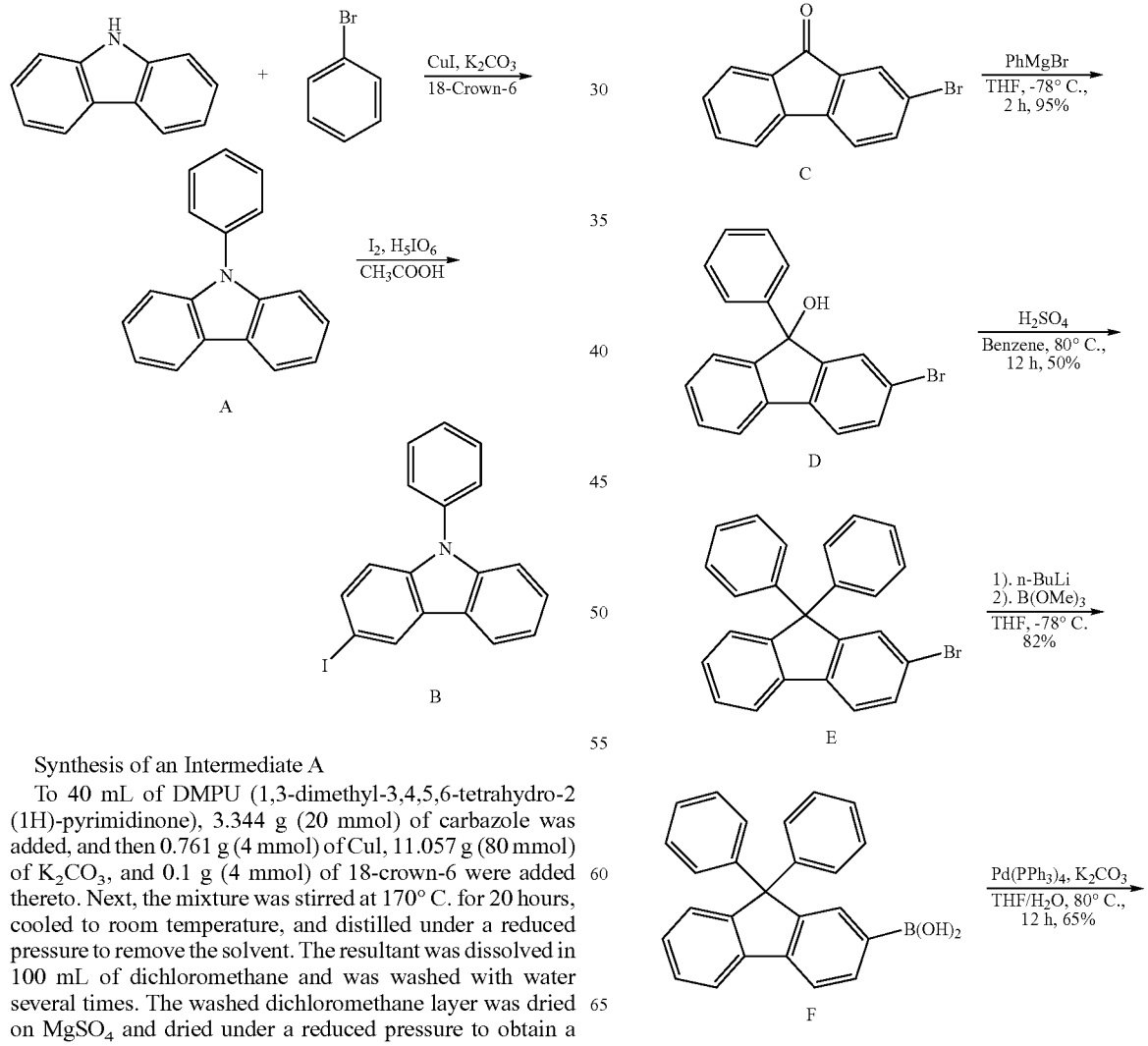

A

B

Synthesis of an Intermediate A

To 40 mL of DMPU (1,3-dimethyl-3,4,5,6-tetrahydro-2 (1H)-pyrimidinone), 3.344 g (20 mmol) of carbazole was added, and then 0.761 g (4 mmol) of CuI, 11.057 g (80 mmol) of $K_2CO_3$, and 0.1 g (4 mmol) of 18-crown-6 were added thereto. Next, the mixture was stirred at 170° C. for 20 hours, cooled to room temperature, and distilled under a reduced pressure to remove the solvent. The resultant was dissolved in 100 mL of dichloromethane and was washed with water several times. The washed dichloromethane layer was dried on $MgSO_4$ and dried under a reduced pressure to obtain a crude product. The crude product was separated and purified by column chromatography on silica gel and recrystallized from hexane to obtain 3.28 g (yield 67%) of the intermediate A as a solid.

Synthesis of an Intermediate B

To 100 mL of 80% acetic acid, 2.433 g (10 mmol) of the intermediate A was added, and then 1.357 g (5.35 mmol) of $I_2$ and 0.333 g (1.46 mmol) of $H_5IO_6$ were added thereto in a solid phase. Next, the mixture was stirred under a $N_2$ atmosphere at 80° C. for 2 hours. After the reaction was completed, the resulting product was extracted with ethyl ether (50 mL) three times to collect organic layers. The collected organic layer was dried on $MgSO_4$ and the solvent was evaporated to obtain a residue. The residue was separated and purified by column chromatography on silica gel to obtain 3.23 g (yield 87%) of the intermediate B.

Reaction Scheme 3

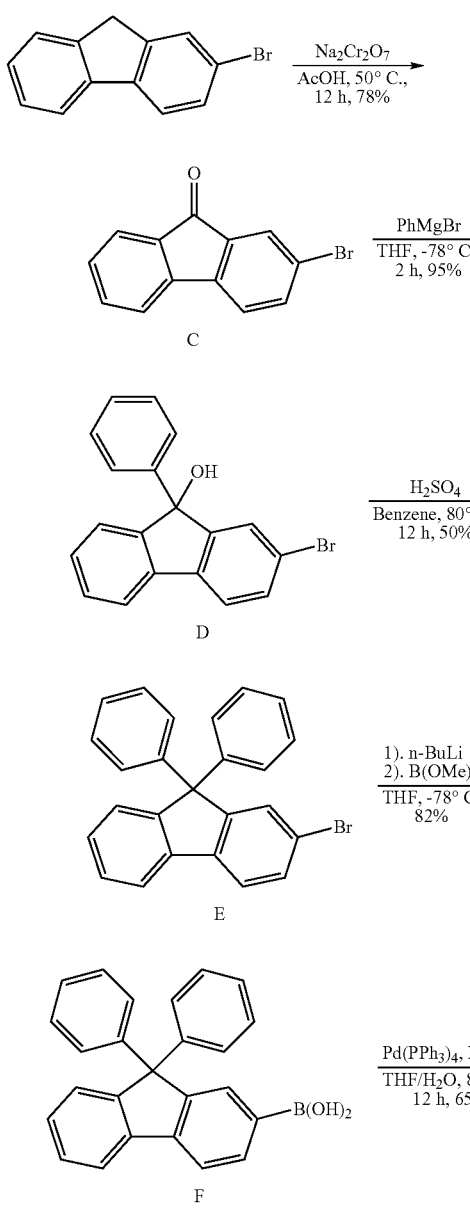

C

D

E

F

-continued

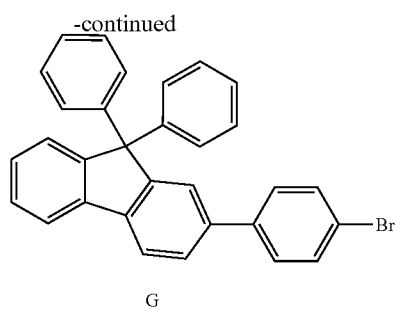

G

Synthesis of an Intermediate C

In 60 mL of acetic acid, 13 g (53 mmol) of 2-bromofluorene was dissolved. 60 g (200 mmol) of sodium bichromate was slowly added to the solution at 0° C. After 12 hours, 200 mL of distilled water was added to the mixture and thoroughly stirred. The resulting yellow solid was filtered and dried to obtain 10 g of the intermediate C (yield 78%).

Synthesis of an Intermediate D

In 60 mL of THF, 8 g (31.6 mmol) of the intermediate C was dissolved. Next, 38 mL (38 mmol) of 1 M phenylmagnesium bromide was slowly added to the solution at −78° C. After 2 hours, the mixture was heated to room temperature and stirred at the same temperature for 5 hours. The resulting was diluted with 50 mL of an aqueous ammonium chloride solution and was extracted three times with ethyl acetate (40 mL) to form organic layers. The collected organic layer was dried on MgSO$_4$ and the solvent was evaporated to obtain a residue. The residue was separated and purified by column chromatography on silica gel to obtain 10 g (yield 95%) of the intermediate D.

The structure of the intermediate D was identified by $^1$H-NMR ((CDCl$_3$, 400 MHz) δ (ppm) 7.64 (d, 1H), 7.54-7.47 (m, 2H), 7.44 (d, 1H), 7.39-7.33 (m, 3H), 730-7.23 (m, 5H), 2.46 (s, 1H)).

Synthesis of an Intermediate E

In 60 mL of benzene and 2.4 mL (45 mmol) of concentrated sulfuric acid that is diluted with a small amount of benzene, 10 g (30 mmol) of the intermediate D was dissolved in. The mixture was stirred at 80° C. for 5 hours and benzene was evaporated to obtain a residue. The residue was made to pH 7 using a 1 M aqueous sodium hydroxide solution, and then extracted three times with 40 mL of ethyl acetate. The collected organic layer was dried on MgSO$_4$ and the solvent was evaporated to obtain a residue. The residue was separated and purified by column chromatography on silica gel to obtain 6 g (yield 50%) of the intermediate E.

Synthesis of an Intermediate F

In 5 mL of THF, 460 mg (1.16 mmol) of the intermediate E was dissolved Next, 0.61 mL (1.5 mmol) of a 2.5 M n-butyl lithium solution in n-hexane was added dropwise to the solution at −78° C. Then, the mixture was stirred for 2 hours. 0.33 mL (2.9 mmol) of trimethyl borate was added to the reaction and stirred at the same temperature for 3 hours and then at room temperature for 12 hours. A 12 M HCl aqueous solution was added to the resulting mixture and stirred at room temperature for 2 hours to form a solution with a pH of 1. Then, the mixture was made to be pH of 14 with a 4 M NaOH aqueous solution and three times extracted with diethyl ether (10 mL) to collect organic layers. The collected organic layer was dried on MgSO$_4$ and the solvent was evaporated to obtain a residue. The residue was separated and purified by column chromatography on silica gel to obtain 345 mg (yield 82%) of the intermediate F as a white solid.

Synthesis of an Intermediate G

In 10 mL of THF, 344 mg (0.95 mmol) of the intermediate F and 560 mg (2.37 mmol) of 1,4-dibromobenzene were dissolved. Next, 22 mg (0.02 mmol) of palladium tetrakistriphenylphosphine was added to the solution. Then, a solution of 660 mg (4.8 mmol) of K$_2$CO$_3$ in 8 mL of distilled water was added to the mixture and stirred at 75° C. for 12 hours.

The mixture was extracted three times with 15 mL of ethyl acetate to collect organic layers. The collected organic layer was dried on MgSO$_4$ and the solvent was evaporated to obtain a residue. The residue was separated and purified by column chromatography on silica gel to obtain 2.90 mg (yield 65%) of the intermediate G. The structure of the intermediate G was identified by $^1$H NMR ($^1$H-NMR (CDCl$_3$, 400 MHz) δ (ppm) 7.79 (dd, 1H), 7.77 (dd, 1H), 7.57 (d, 1H), 7.54 (dd, 1H), 7.49 (dd, 2H), 7.42-7.37 (m, 3H), 7.35 (dd, 1H), 7.27 (dt, 1H), 7.25-7.19 (m, 10H)) and $^{13}$C-NMR ($^{13}$C-NMR (CDCl$_3$, 100 MHz) δ (ppm) 152.0, 151.8, 145.8, 140.2, 139.8, 139.6, 139.5, 131.8, 128.7, 128.3, 128.1, 127.9, 127.6, 126.7, 126.5, 126.3, 124.7, 120.5, 120.3, 65.6).

Reaction Scheme 4

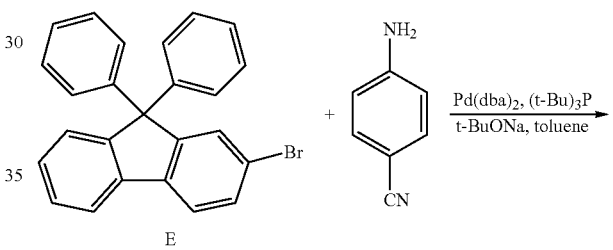

E

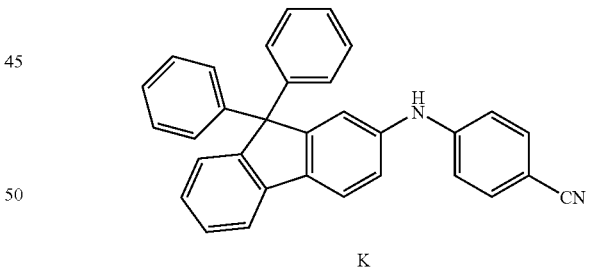

K

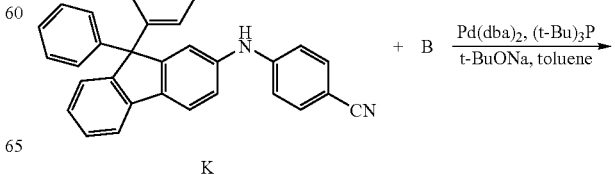

K

-continued

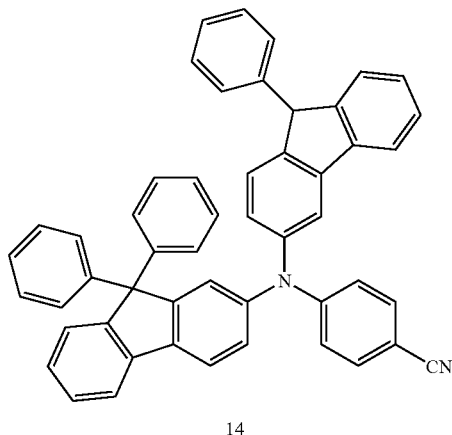

14

Synthesis of an Intermediate K

In 5 mL of toluene and 0.144 g (1.5 mmol) of t-BuONa, 340 mg (0.856 mmol) of the intermediate E and 142 mg (1.2 mmol) of 4-aminobenzonitrile were dissolved, 0.018 g (0.02 mmol) of Pd(dba)2 and 0.004-0.006 g (0.02-0.03 mmol) of (t-Bu)3P were added thereto, and then stirred at 80° C. for 5 hours. The reaction was extracted three times with 20 mL of ethyl ether to collect organic layers. The collected organic layer was dried on $MgSO_4$ and the solvent was evaporated to obtain a residue. The residue was separated and purified by column chromatography on silica gel to obtain 0.27 g (yield 73%) of the intermediate K.

Synthesis of the Compound 14

In 10 mL of toluene, 267 mg (0.614 mmol) of the intermediate K and 0.332 g (0.9 mmol) of the intermediate B were dissolved. Next, 0.144 g (1.5 mmol) of t-BuONa, 0.018 g (0.02 mmol) of Pd(dba)2 and 0.004-0.006 g (0.02-0.03 mmol) of (t-Bu)3P were added to the solution and then stirred at 90° C. for 6 hours.

The reaction mixture was extracted three times with 30 mL of ethyl ether to collect organic layers. The collected organic layer was dried on $MgSO_4$ and the solvent was evaporated to obtain a residue. The residue was separated and purified by column chromatography on silica gel to obtain 0.236 g (yield 57%) of the compound 14. The structure of the compound 14 was identified by $^1$H-NMR($^1$H-NMR ($CDCl_3$, 400 MHz) δ (ppm) 7.97 (d, 1H), 7.90 (d, 1H), 7.69 (d, 1H), 7.65 (d, 1H), 7.60 (d, 2H), 7.56 (dd, 2H), 7.48 (m, 1H), 7.40 (d, 2H), 7.35 (m, 6H), 7.24 (m, 3H), 7.16 (m, 10H), 7.11 (dd, 1H), 6.93 (d, 2H))

EXAMPLE 1

A ITO glass substrate (Corning Co, surface resistance: 15 $Ω/cm^2$, thickness: 1200 Å) was cut to a size of 50 mm×50 mm×0.7 mm to form an anode. Next the substrate was ultrasonically cleaned in isopropyl alcohol and pure water each for 5 minutes, then irradiated with UV light for 30 minutes, exposed to ozone, and washed. Then, the glass substrate was placed on a vacuum evaporator.

IDE406 (available from Idemitsu) was vacuum evaporated on the glass is substrate to form an HIL having a thickness of 600 Å. Then, 4,4'-bis[N-(1-naphthyl)-N-phenylamino]biphenyl (NPB) was vacuum evaporated to a thickness of 300 Å on the HIL to form an HTL.

Subsequently, a mixture of the compound 14 as a phosphorescent host and Ir(ppy)3 as a green phosphorescent dopant in a weight ratio of 93:7 was deposited on the HTL to form an EML with a thickness of 300 Å. Alq3 was deposited on the EML to form an ETL having a thickness of 300 Å. LiF was deposited on the ETL to form an EIL having a thickness of 10 Å and Al was deposited on the EIL to form a cathode having a thickness of 3000 Å, thereby completing an OEL device.

A color coordinate, a luminance, luminous efficiency and the like of the OEL device were measured. As a result, it was found that the OEL device had a current density of 31.46 $mA/cm^2$, a luminance of 2,000 $cd/m^2$, a color coordinate of (0.30, 0.60), and a luminous efficiency of 6.5 cd/A at a DC voltage of 6V.

COMPARATIVE EXAMPLE 1

An OEL device was prepared in the same manner as in Example 1, except that a mixture of CBP as a phosphorescent host and Ir(ppy)3 as a green phosphorescent dopant at a weight ratio of 93:7 was deposited on the HTL to form an EML.

A color coordinate, a luminance, luminous efficiency and the like of the OEL device were measured. As a result, it was found that the OEL device had a current density of 5.17 $mA/cm^2$, a luminance of 1,168 $cd/m^2$, a color coordinate of (0.30, 0.60), and a luminous efficiency of 22.4 cd/A at a DC voltage of 6 V.

Figure 2:
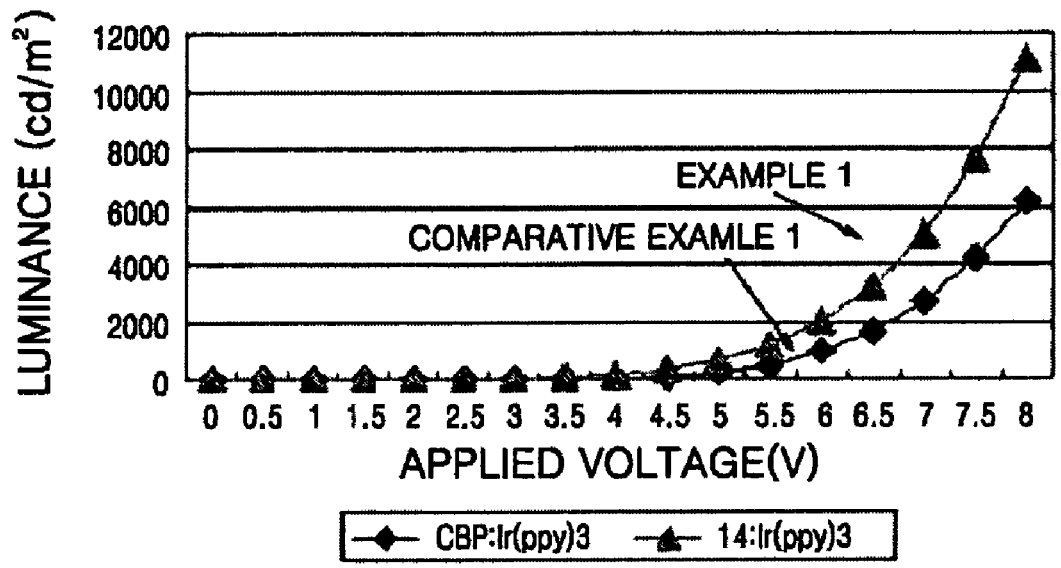
FIG. 2 is a graph illustrating the relationship between the voltage and the luminance of OEL devices prepared according to Example 1 of the present invention and Comparative Example 1.

It can be seen from the above results that when the compound 14 according to the present invention is used as the green phosphorescent host, the turn-on voltage was lowered by as much as 1 V due to a remarkable improvement in charge transport ability and the significant increase in luminance at the same turn-on voltage. FIG. 2 shows that Example 1 using the compound 14 has a turn-on voltage that is lower than that of Comparative Example 1 and shows a higher luminance at the same turn-on voltage.

EXAMPLE 2

A ITO glass substrate (Corning Co, surface resistance: 15 $Ω/cm^2$, thickness: 1200 Å) was cut to a size of 50 mm×50 mm×0.7 mm to form an anode. Next, the substrate was ultrasonically cleaned in isopropyl alcohol and pure water each for 5 minutes, irradiated with UV light for 30 minutes, exposed to ozone, and washed. Then, the glass substrate was placed on a vacuum evaporator. IDE406 was vacuum evaporated on the glass substrate to form an HIL having a thickness of 600 Å. Then, NPB was vacuum evaporated to a thickness of 300 Å on the HIL to form an HTL. Subsequently, a mixture of the compound 14 as a phosphorescent host and RD61 (available from UDC) as a red phosphorescent dopant at a weight ratio of 90:10 was deposited on the HTL to form an EML having a thickness of 300 Å.

Alq3 was then deposited on the EML to form an ETL with a thickness of 300 Å. LiF was deposited on the ETL to form an EIL having a thickness of 10 Å and Al was deposited on the EIL to form a cathode having a thickness of 3000 Å, thereby completing an OEL device.

A color coordinate, a luminance, luminous efficiency and the like of the OEL device were measured. As a result, it was found that the OEL device had a current density of 23.44 mA/cm$^2$, a luminance of 1,979 cd/m$^2$, a color coordinate of (0.62, 0.38), and a luminous efficiency of 8.44 cd/A at a DC voltage of 5 V.

COMPARATIVE EXAMPLE 2

An OEL device was prepared in the same manner as in Example 1, except that a mixture of CBP as a phosphorescent host and RD61 as a red phosphorescent dopant at a weight ratio of 90:10 was deposited on the HTL to form an EML.

For the OEL device, a color coordinate, a luminance, luminous efficiency and the like were measured. As a result, it was found that the OEL device had a current density of 4.27 mA/cm$^2$, a luminance of 423.3 cd/M$^2$, a color coordinate of (0.62, 0.38), and a luminous efficiency of 9.92 cd/A at a DC voltage of 5 V.

Figure 3:
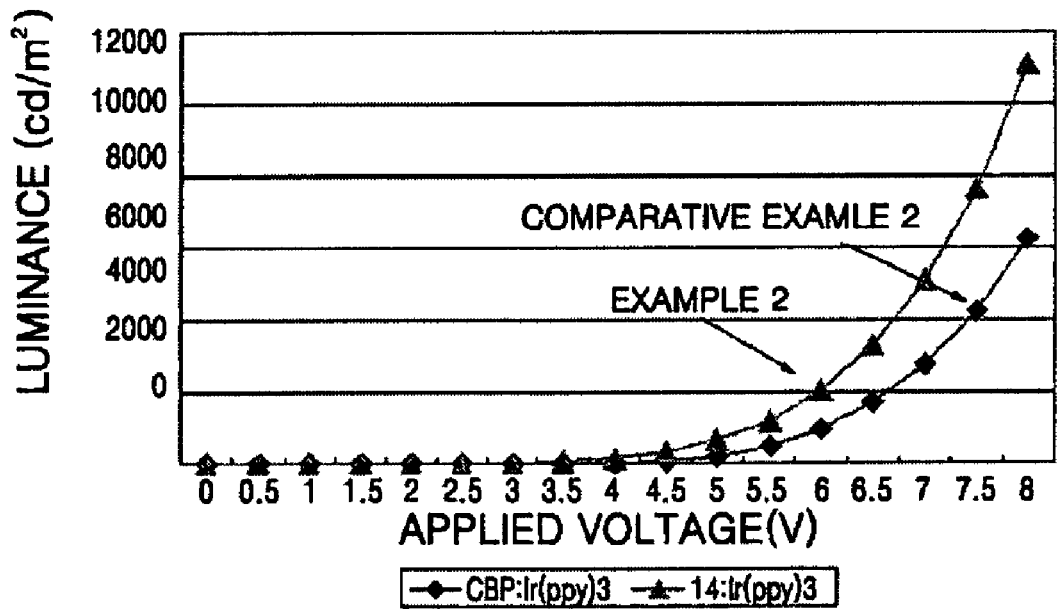
FIG. 3 is a graph illustrating the relationship between the voltage and the luminance of OEL devices prepared according to Example 2 of the present invention and Comparative Example 2.

It can be seen from the above results that when the compound 14 according to the present invention is used as a red phosphorescent host, the turn-on voltage was lowered by as much as 0.5 V due to a remarkable improvement in charge transport ability and a significant increase in the luminance at the same turn-on voltage. Unlike when the compound 14 is used as a green phosphorescent host, the luminous efficiency is not significantly decreased, and thus relatively better results can be obtained. FIG. 3 shows that Example 2 using the compound 14 has a turn-on voltage lower than that of Comparative Example 2 and shows a higher luminance at the same turn-on voltage.

Figure 4:
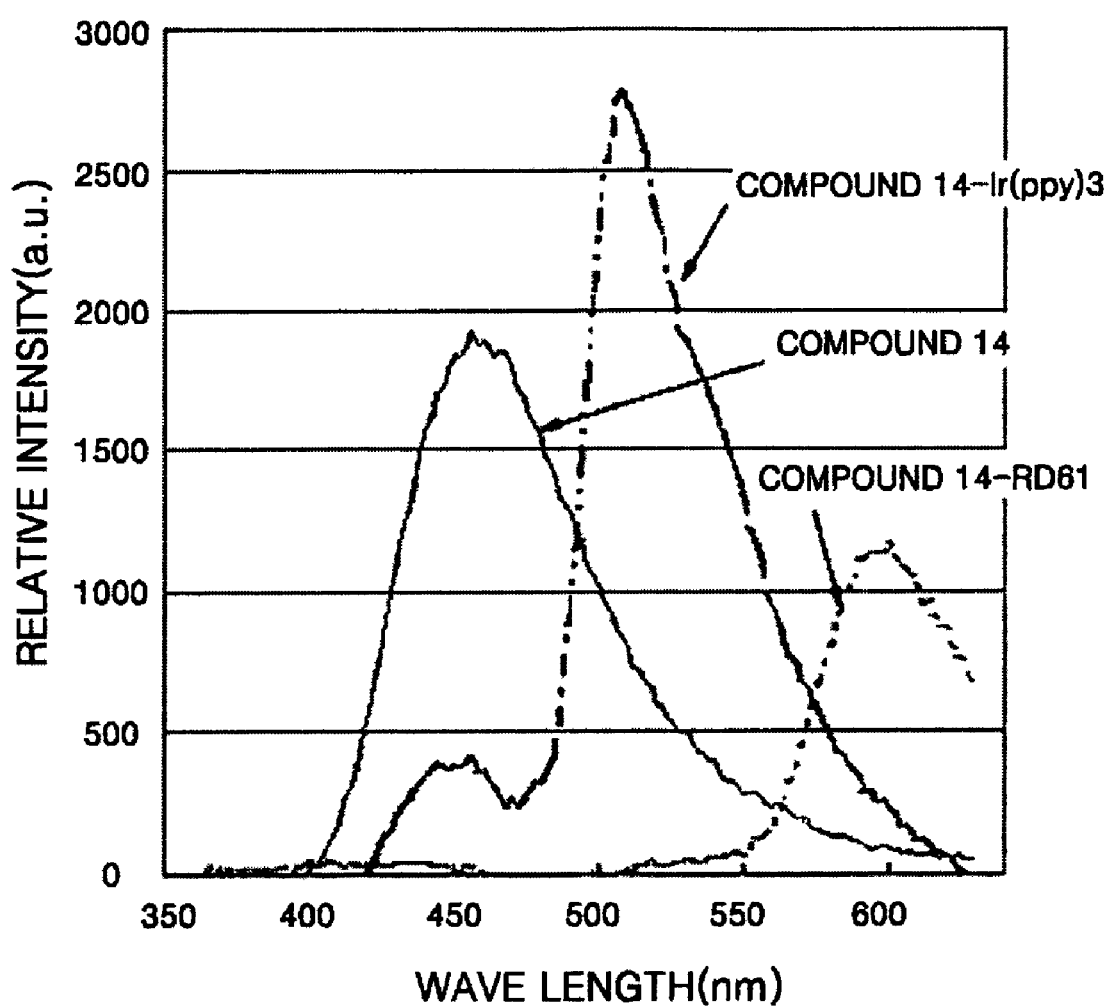
FIG. 4 is photoluminescence (PL) spectrum of OEL compounds according to the present invention.

In addition, a mixture of the compound 14 and polymethylmethacrylate (PMMA) at a weight ratio of 15:1 was dissolved in chloroform and spin coated on a glass substrate (50 mm×50 mm×1.0 mm) to form a thin film. The PL spectrum of the thin film was measured. As a result, a highest PL peak occurred at 456 nm as shown in FIG. 4.

A mixture of the compound 14 and PMMA at a weight ratio of 15:1 was dissolved in chloroform and a red phosphorescent dopant Ir(ppy)3 was added thereto. The resulting solution was then spin coated on a glass substrate (50 mm×50 mm×1.0 mm) to form a thin film. The PL spectrum of the thin film was measured as shown in FIG. 4. It can be seen from the PL spectrum that an energy transition in the thin film state occurs easily.

Similarly, 5 parts by weight of phosphorescent dopant RD61 was dissolved in a PMMA polymer solution of the compound 14 and spin coated on a glass substrate to form a thin film. The PL spectrum of the thin film was measured. It can be seen from the PL spectrum in FIG. 4 that an energy transition in the thin film state occurs easily.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A fluorene-based compound represented by one of Formulas 33-37:

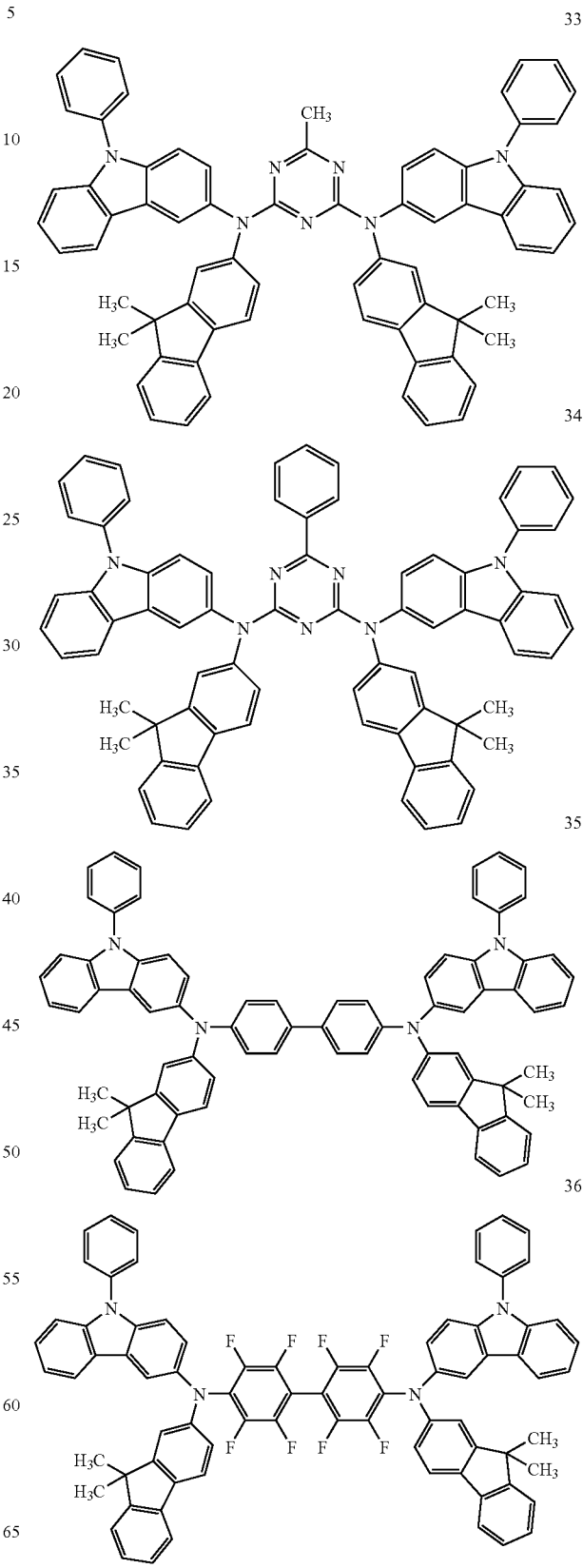

-continued

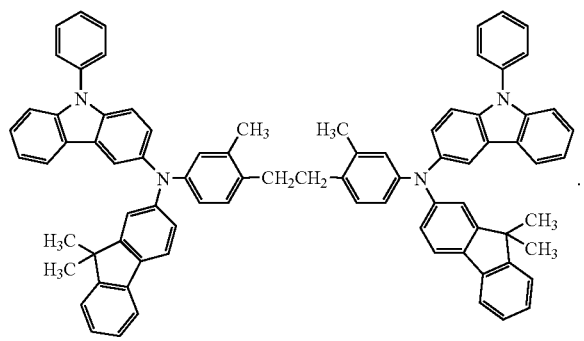

2. An organic electroluminescent display device, comprising:
   two electrodes; and
   an organic layer interposed between the electrodes,
   wherein the organic layer comprises the fluorene-based compound of claim 1.

3. The organic electroluminescent display device of claim 2, wherein the organic layer is an emission layer, a hole injection layer or a hole transport layer.

4. The organic electroluminescent display device of claim 2, wherein the organic layer is the emission layer.

5. The organic electroluminescent display device of claim 4, wherein the fluorene-based compound is used as fluorescent and phosphorescent hosts for blue, green and red fluorescent and phosphorescent dopants.

* * * * *